United States Patent
Siegel et al.

(10) Patent No.: US 10,524,733 B2
(45) Date of Patent: Jan. 7, 2020

(54) METHOD FOR IMPROVING THE SIGNAL TO NOISE RATIO OF A WAVE FORM

(71) Applicant: United States Army Research Laboratory ATTN:RDRL-LOC-I, Adelphi, MD (US)

(72) Inventors: David Siegel, Cincinnati, OH (US); Canh Ly, Laurel, MD (US); Troy Lau, Ann Arbor, MI (US); William D. Hairston, Churchville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 828 days.

(21) Appl. No.: 14/257,110

(22) Filed: Apr. 21, 2014

(65) Prior Publication Data

US 2015/0297141 A1   Oct. 22, 2015

(51) Int. Cl.
| | |
|---|---|
| *A61B 5/00* | (2006.01) |
| *A61B 5/0476* | (2006.01) |
| *G06K 9/00* | (2006.01) |

(52) U.S. Cl.
CPC .......... *A61B 5/7203* (2013.01); *A61B 5/0476* (2013.01)

(58) Field of Classification Search
CPC ........ G06K 9/00516; A61B 5/00; G06F 19/00
See application file for complete search history.

(56) References Cited

U.S. PATENT DOCUMENTS

| 4,705,049 A | 11/1987 | John | |
|---|---|---|---|
| 2007/0071327 A1* | 3/2007 | Akiyama | G06K 9/00516 382/207 |
| 2008/0183466 A1* | 7/2008 | Nongpiur | G10L 19/0216 704/226 |
| 2012/0172744 A1* | 7/2012 | Kato | A61B 5/0478 600/544 |

OTHER PUBLICATIONS

Alfred Mertins, "Signal Analysis: Wavelets, Filter Banks, Time-Frequency Transforms and Applications", 1999. pp. 210-264 (Year : 1999).*

(Continued)

*Primary Examiner* — Alexander Satanovsky
*Assistant Examiner* — Brent A. Fairbanks
(74) *Attorney, Agent, or Firm* — Robert Thompson; Eric B. Compton

(57) ABSTRACT

A method for improving the signal to noise ratio of an EEG signal in which a wavelet packet decomposition having a plurality of levels is first applied to a time slice of the EEG signal. A default signal is set to the first wavelet packet and a default peak response is then calculated for the first wavelet node. An update signal is set to the default signal combined with another of the wavelet nodes and an update peak response signal is then calculated of the update signal. If the update peak response signal exceeds the default peak response, the default peak response is set equal to the update peak response and the default signal is set equal to the update signal. Otherwise, the value of the current node is set to zero which effectively eliminates the signal data of the current wavelet node. These steps are reiterated for all of the wavelet nodes and, thereafter, a composite waveform of the EEG signal is reconstructed from the non-zero wavelet nodes.

6 Claims, 1 Drawing Sheet

(56) References Cited

OTHER PUBLICATIONS

Robi Polikar, The Wavelet Tutorial, 2001, Second Edition (Year: 2001).*

T. Demiralp, A. Ademoglu, Y. Istefanopulos, C.B. Eroglu, E. Basar, "Wavelet Analysis of OddBall P300," International Journal of Psychophysiology, vol. 39, pp. 221-227, 2001.

R.Quian Quiroga, and H. Garcia, "Single-Trial Event Related Potentials with Wavelet Denoising," Clinical Neurophysiology, vol. 114, pp. 376-390, 2003.

V. Krishnaveni, S. Jayaraman, L. Anitha, and K. Ramadoss, "Removal of Ocular Artifacts from EEG Using Adaptive Thresholding of Wavelet Coefficients," Journal of Neural Engineering, vol. 3, pp. 338-346, 2006.

Z. Wu, J. Wang, D. Shen, and X. Bai, "Denoising of Event-Related Potential Signal Based on Wavelet Method, Life System Modeling and Intelligent Computing," Lecture Notes in Computer Science, vol. 6330, pp. 165-172, 2010.

E. Causevic, R.E. Morley, "Fast Wavelet Estimation of Weak Biosignals," IEEE Transactions on Biomedical Engineering, vol. 52, pp. 1021-1032, 2005.

R. Quian Quiroga, "Obtaining Single-Stimulus Evoked Potentials with Wavelet Denoising," Physica D, vol. 145, pp. 278-292, 2000.

E.A. Bartnik, K.J. Blinowska, and P.J. Durka, "Single Evoked Potential Reconstruction by Means of Wavelet Transform Biological Cybernetics," vol. 67, pp. 175-181, 1992.

A. Jacquin, E. Causevic, R. John, and J. Kovacevic, "Adaptive Complex waveletbased filtering of EEG for extraction of evoked potential responses, IEEE International Conference on Acoustics," Speech, and Signal Processing, pp. 393-396, 2005.

* cited by examiner

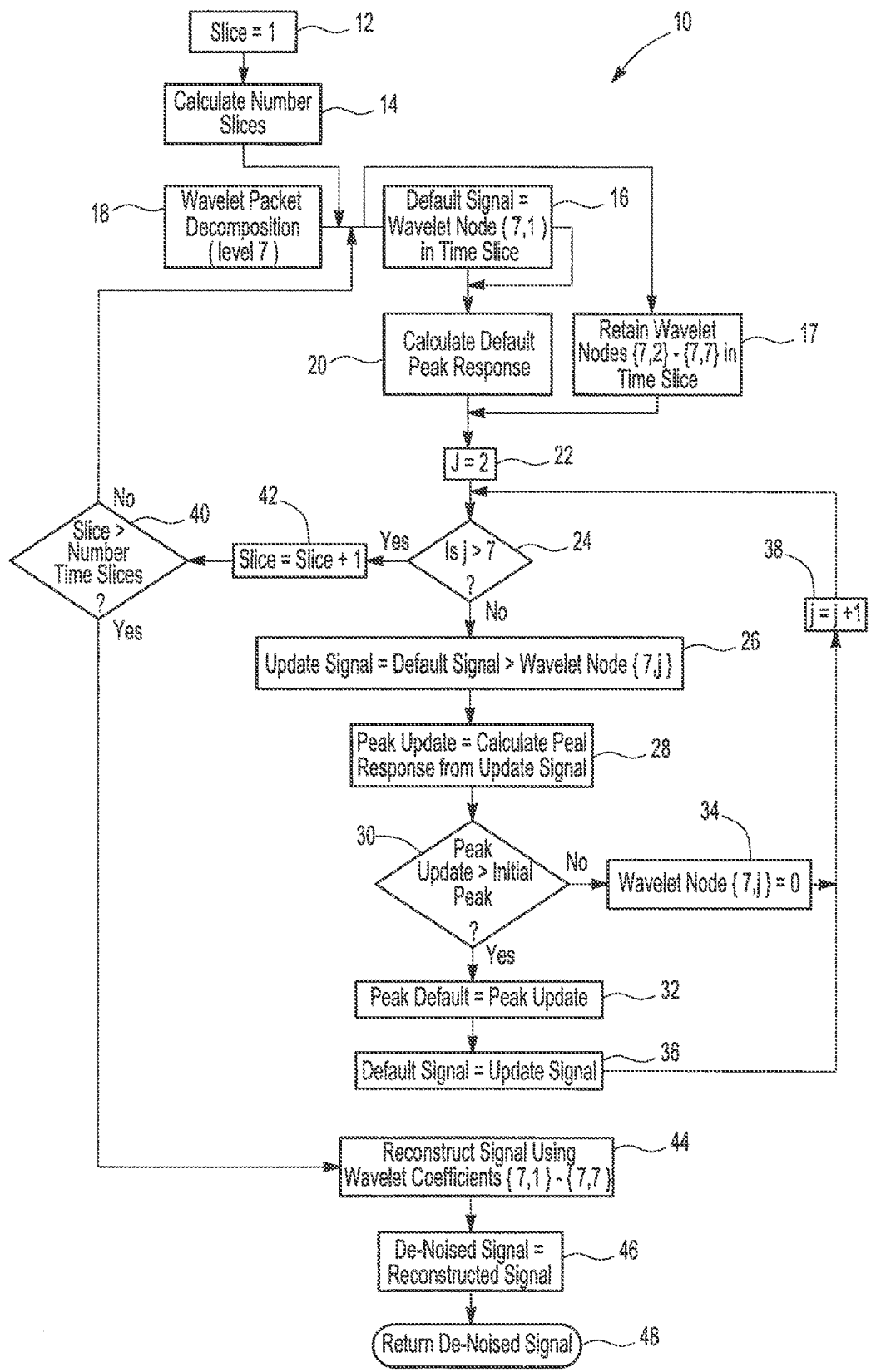

METHOD FOR IMPROVING THE SIGNAL TO NOISE RATIO OF A WAVE FORM

GOVERNMENT INTEREST

The embodiments described herein may be manufactured, used, and licensed by or for the United States Government without the payment of royalties thereon.

BACKGROUND

Technical Field

The present invention relates generally to a method for improving the signal to noise ratio of a waveform and, more particularly, to a method for improving the signal to noise ratio of an EEG signal.

Description of Related Art

In many situations, it is desirable to monitor electroencephalography (EEG) signals. For example, hospitals and other medical facilities often utilize EEG monitors to monitor the EEG signals. Additionally, in military applications it is oftentimes desirable to monitor the EEG signals of warriors in a combat arena.

It is well known that under certain circumstances, the human brain responds to certain stimuli in a manner that yields a large-amplitude response with a latency of approximately 300 milliseconds. This signal, known as the P300 response for EEG signal analysis, is considered to be one of the most important EEG signals when assessing the reaction of the brain to a stimulus. Furthermore, even though the P300 response begins around 300 milliseconds following the stimulus for most individuals, the P300 response actually extends between 300 and 600 milliseconds after the stimulus, and is highly variable across individuals and circumstances.

One difficulty in monitoring EEG signals such as the P300 response, however, is that such signals are relatively noisy and, thus, difficult to properly analyze. Indeed, in some situations the signal noise may obscure the P300 EEG waveforms to such a degree that it is difficult to identify or accurately analyze the P300 signal.

There have been previously known attempts to apply noise filtering to the EEG signal in an attempt to improve the signal to noise ratio of the EEG signal and, in particular, the P300 response. These previously known attempts to improve the signal to noise ratio, however, have always focused on applying a static noise filter to sequential time segments of the EEG signal over the entire duration of the signal e.g. 300-600 milliseconds. A disadvantage of this approach, however, is that the noise present on the P300 response signal varies over time even as short as 300 milliseconds-600 milliseconds. Thus, while the noise filter of these previously known methods may improve the signal to noise ratio of the EEG signal over a portion of the 300-600 millisecond time period, they provide minimal, if any, improvement of the signal to noise ratio over other portions of the 300-600 millisecond P300 signal.

SUMMARY

The present invention provides a processor implemented method for improving the signal to noise ratio of single trial EEG signals which overcomes the disadvantages of the previously known methods and processes. Furthermore, the method of the present invention automatically adapts for different sequential time segments or time slices over the entire duration of the EEG signal.

In brief in the method of the present invention, a single trial of EEG response, such as the P300 signal beginning at 300 milliseconds following a stimulus, is first acquired. A wavelet packet decomposition of N levels is then applied to the acquired EEG signal to form N wavelets of adjacent frequency pass bands, e.g. 0-2 hertz, 2-4 hertz, . . . 12-14 hertz. Each wavelet has a high pass and low pass coefficient or node corresponding to signal magnitude and direction. In the preferred embodiment of the invention, N is equal to 7, which refers to the level 7 of decomposition of the wavelet packet, although fewer or more wavelet packets may be utilized without deviation from the spirit or scope of the invention.

A default signal is then set to the first wavelet node or coefficient. A calculated default peak response of the first wavelet node is then also calculated.

An update signal is then set to the default signal combined with a signal from another of the wavelet nodes and an update peak response signal is then calculated from the update signal. If the update peak response signal exceeds the default peak response, indicative of an improvement of the signal to noise ratio, the default peak response is then set to the update peak response and the default signal is set equal to the update signal. Otherwise, indicative that no improvement in the signal to noise ratio was obtained, the coefficient of another wavelet node is set to zero effectively deleting that wavelet node and its signal information from the wavelet packet.

The above steps are then reiterated for all of the wavelet nodes. Following the processing of all of the wavelet nodes, at least one node or coefficient and up to a maximum of N wavelet nodes, are set to a non-zero value. A waveform of the de-noised EEG signal is then formed by reconstructing the EEG signal from all of the non-zero wavelet nodes.

In order to analyze the entire EEG signal, the above process is repeated for a plurality of sequential time segments or time slices. However, unlike the previously known methods to improve the signal to noise ratio of EEG signals, the wavelet coefficients for each time slice are recalculated and applied to the decomposed signal so that the method of the present invention adapts to the requirements for noise reduction of the EEG signal for each time slice over the entire period of analysis. As such, the method of the present invention is able to significantly improve the signal to noise ratio of the EEG signal despite variations of the signal and noise over the analysis period.

BRIEF DESCRIPTION OF THE DRAWING

A better understanding of the present invention will be had upon reference to the following detailed description when read in conjunction with the drawing which is a flowchart illustrating the method of the present invention.

DETAILED DESCRIPTION

A flowchart or algorithm 10 illustrating a preferred embodiment of the method of the present invention is shown in the drawing. The flowchart 10, which will be described in greater detail, is performed by a programmed processor or programmed computer. Any conventional processor may be employed.

The method of the present invention begins at step 12 in which the time segment or time slice is set to an initial value of one. Step 12 then proceeds to step 14 where the number of time segments is calculated or set by the program. The number of time slices calculated or set at step 14 will vary depending upon the overall duration of the EEG signal to be processed by the method of the present invention. For example, a relatively large number of time slices will be set for an EEG signal of relatively long duration and vice versa. Step 14 then proceeds to step 16.

Contemporaneous with the calculation of the number of time slices, an EEG signal corresponding to the first time slice as set in step 12 is first processed by applying a wavelet packet decomposition at step 18. Preferably, the wavelet packet decomposition performed at step 18 comprises a seven level decomposition. However, the wavelet packet decomposition may have fewer or more levels than seven without deviation from the spirit or scope of the invention.

In the well known fashion, the wavelet decomposition performed at step 18 effectively forms a series of adjacent bandwidth filters which separates the acquired EEG waveform in the first time slice into nodes or coefficients of adjacent frequency pass bands. For example, in a seven level or seven node wavelet packet decomposition, the first wavelet node will contain the EEG signal between 0 and 2 hertz, the second wavelet node will contain the EEG signal between 2 and 4 hertz, and so on with the seventh node of the decomposed wavelet packet containing the EEG signal corresponding to 12-14 hertz. The node or coefficient corresponds to the magnitude of the EEG signal within its pass band as well as a vector or direction of the EEG signal. Step 18 then proceeds to step 16.

At step 16, a default signal is then first set equal to the first wavelet node in the current time slice. Step 16 then proceeds to step 20.

At step 20, a default peak response is calculated for the default signal set at step 16. Although the default signal peak response may be set to equal the peak response in the default wavelet, preferably the default peak response is calculated from a ratio of the peak response to the root mean square of the default signal. Step 20 then proceeds to step 22. Furthermore, contemporaneously with steps 16 and 20, step 17 retains all of the other or nonprocessed wavelet nodes.

At step 22, the wavelet node number is incremented, i.e. set to the value of 2. Furthermore, all of the other wavelet nodes, namely packet nodes 2-7, are retained from the wavelet packet decomposition at step 18 by step 17. Consequently, when the wavelet node is set to 2 by step 22, all remaining wavelet nodes are accessible to the method. Step 22 then proceeds to step 24.

At step 24, the method or program first tests to determine if the node number is greater than seven, i.e. whether or not the entire wavelet has been processed, by comparing the wavelet node number j to the level of the wavelet packet decomposition which was set to 7 by step 18 in the instant example. Since two is less than the total number of wavelet nodes, step 24 proceeds to step 26.

At step 26, an update signal is created and set equal to the default signal obtained at step 16 combined with the current wavelet node which is initially set by step 22 as the second node. Consequently, on the first iteration through step 26, the update signal is equal to the combination of the first two wavelet nodes, namely nodes 1 and 2. Step 26 then proceeds to step 28.

At step 28, a peak update is calculated from the update signal determined at step 28. Although the peak update may be an absolute value of the peak response of the update signal, preferably, the peak update is calculated from the ratio of the peak response to the root-mean-square (RMS) value of the combined update signal. Step 28 then proceeds to step 30.

At step 30, the peak update calculated at step 28 is compared with the initial default peak response calculated at step 20. If the peak update calculated by step 28 exceeds the default peak response from step 20, step 30 proceeds to step 32. Otherwise, step 30 proceeds to step 34.

Even though step 26 combines the default signal with the current wavelet node, the current wavelet node may have a negative value. As such, the update signal calculated at step 26 as well as the peak update calculated at step 28 may be either greater or less than the original update signal.

Assuming that the peak update calculated at step 28 exceeds the initial or default peak response, step 30 proceeds to step 32 where the peak default response is set equal to, i.e. replaced by, the peak update calculated at step 28. Step 32 then proceeds to step 36 where the default signal is set to the update signal determined at step 26. Step 36 then proceeds to step 38 where the wavelet node number j is incremented.

Conversely, in the event that the peak update calculated at step 28 is less than the default peak response calculated at step 20, step 30 instead proceeds to step 34 where the current wavelet node, i.e. node 2 for the first iteration, is set to zero. Setting the current node or coefficient to zero effectively eliminates the signal data for the frequency pass band for the current wavelet node. Step 34 then proceeds to step 38.

Step 38 then proceeds back to step 24 with the node number incremented by step 38 where the above process is reiterated for each of the wavelet nodes until the wavelet node number j is greater than 7, i.e. the decomposition level set at step 18. When this occurs, step 24 branches to step 40 instead of step 26.

Consequently, it can be seen that by retaining the signal data for only the wavelet nodes that improve the overall EEG signal by increasing the peak default response of the overall EEG signal, and effectively eliminating the signal data for all other wavelet nodes, the resulting wavelet contains at least one, but no more than seven nodes having a non-zero value. Furthermore, the nodes containing a non-zero coefficient each represent a known frequency pass band for the EEG signal.

At step 40, the number of time slices is incremented and step 40 then proceeds to step 42. At step 42, the number of time slices following the increment by step 40 is compared with the number of time slices calculated or set at step 14. If more time slices must be processed, step 42 branches back to step 16, a new wavelet packet decomposition is performed on the acquired EEG signal in the next time slice, and the previously described process is reiterated for the next time slice.

Conversely, if all of the time slices determined by step 14 have been processed, step 42 instead branches to step 44 where the EEG signal is reconstructed using the non-zero wavelet nodes for each of the time slices. Step 44 then proceeds to step 46 where the now reconstructed and de-noised EEG signal is set to the reconstructed signal performed at step 44. Step 46 then proceeds to step 48 and returns the de-noised signal.

As can be seen from the foregoing, the nodes of the wavelet decomposition for a particular time slice effectively act as band pass filters for adjacent frequency ranges and, by setting the coefficient or node equal to zero for the wavelet nodes which do not improve the overall signal, i.e. de-noise the signal, the ultimately reconstructed signal improves the signal to noise ratio of the EEG signal.

Furthermore, the coefficients or nodes of the wavelet are set individually for each time slice in an automated and adaptive fashion. Thus, the non-zero nodes or coefficients for each wavelet will vary between different time slices for the processed EEG signal thus producing a de-noised signal over a time period determined by the number of time slices and in which the signal processing adapts automatically to each different time slice.

Preferably, wavelet transforms are used to filter the acquired EEG signal, or other signal, into adjacent pass band frequency segments. However, other conventional methods may be used to so filter the acquired signal without deviation from the spirit or scope of the invention.

From the foregoing, it can be seen that the present invention provides an effective method for processing signals and, in particular, for processing EEG signals. Having described my invention, however, many modifications thereto will become apparent to those skilled in the art to which it pertains without deviation from the spirit of the invention as defined by the scope of the appended claims.

We claim:

1. A method for improving the signal to noise ratio of a single trial electroencephalogram (EEG) signal waveform for an individual comprising:
   performing with a signal processor computer operatively associated with an EEG monitoring system the steps of:
   a) acquiring the single trial EEG signal waveform for the individual from the EEG monitoring system, wherein the waveform is an electrical signal providing a measurement of voltage fluctuations resulting from ionic current within the neurons of the individual's brain and comprises a Peak amplitude (P300) response of 300 to 600 milliseconds which follows the individual's brain response to a stimulus,
   b) applying a wavelet packet decomposition to said waveform to form adjacent wavelet nodes of adjacent frequency pass bands, each node having a set of coefficients corresponding to the magnitude of the P300 response of the EEG signal within its pass band,
   c) constructing a default signal from the set of first wavelet node coefficients,
   d) calculating a default peak response of said first wavelet node by calculating the ratio of the peak value of the magnitude of said default signal and the root-mean-square of the default signal,
   e) constructing a signal using the set of coefficients from the next wavelet node of said wavelet nodes,
   f) setting an update signal to the default signal combined with the signal constructed from the set of coefficients from the next wavelet node,
   g) calculating an update peak response of said update signal by calculating the ratio of the peak value of the magnitude of said update signal and the root-mean-square value of the update signal,
   h) if the update peak response exceeds said default peak response, setting said default peak response equal to said update peak response and said default signal equal to said update signal, otherwise setting the set of coefficients from the next wavelet node to zero,
   i) reiterating steps e) through g) for all remaining of said wavelet nodes, and
   j) thereafter, reconstructing a composite waveform from said updated wavelet nodes to form an improved single trial EEG signal waveform that is an electrical signal having an improved signal to noise ratio compared to the single trial EEG signal waveform initially acquired by the EEG monitoring system.

2. The method as defined in claim 1 and comprising the step of reiterating said method over a plurality of sequential time periods.

3. The method as defined in claim 1, wherein the number of frequency pass bands is 7.

4. A method for improving the signal to noise of a single trial electroencephalogram (EEG) signal waveform for an individual comprising:
   performing with a signal processor computer operatively associated with an EEG monitoring system the steps of:
   a) acquiring the single trial EEG signal waveform for the individual from the EEG monitoring system, wherein the waveform is an electrical signal providing a measurement of voltage fluctuations resulting from ionic current within the neurons of the individual's brain and comprises a Peak amplitude (P300) response,
   b) dividing said waveform into a plurality of adjacent frequency band segments at a selected time, each frequency band segment comprising a plurality of nodes having a set of coefficients corresponding to the magnitude of the P300 response of the EEG signal,
   c) constructing a default signal from the set of coefficients of the first band segment,
   d) calculating a default peak response of said default signal,
   e) constructing a signal using the set of coefficients from the next wavelet node of said wavelet nodes,
   f) creating an update signal equal to said default signal combined with the waveform constructed from the set of coefficients for the next band segment,
   g) calculating a peak update response of said update signal,
   h) if the peak update response exceeds said default peak response, setting said default signal to said update signal and said default peak response to said peak update response, and otherwise disregarding the set of coefficients from the next wavelet node for said band segment,
   i) reiterating steps e) through g) for all remaining of said band segment nodes, and
   j) reconstructing a composite waveform from the updated band segment nodes to form an improved single trial EEG signal waveform that is an electrical signal having an improved signal to noise ratio compared to the single trial EEG signal waveform initially acquired by the EEG monitoring system.

5. The method as defined in claim 4 and comprising the step of reiterating said method over a plurality of sequential time periods.

6. The method as defined in claim 4 wherein said default setting step comprises the step of calculating the ratio of the peak value of said default signal and the root mean square of the default signal.

* * * * *